United States Patent [19]

Barreau et al.

[11] Patent Number: 4,831,034
[45] Date of Patent: May 16, 1989

[54] 4-BENZYLPIPERAZINES USEFUL AS NEUROLEPTICS

[75] Inventors: Michel Barreau, Montgeron; Marie-Therese Comte, Chevilly Larue; Jean-Luc Malleron, Les Ulis; Gerard Ponsinet, Sucy en Brie, all of France

[73] Assignee: Rhone-Poulenc Sante, Courbevoie, France

[21] Appl. No.: 84,035

[22] Filed: Aug. 11, 1987

[30] Foreign Application Priority Data

Aug. 12, 1986 [FR] France ................................ 86 11617

[51] Int. Cl.⁴ ................ A61K 31/495; A61K 31/505; C07D 295/02; C07D 295/04
[52] U.S. Cl. .................................... 514/255; 514/248; 514/249; 544/280; 544/281; 544/350; 544/360; 544/368; 544/402
[58] Field of Search ............... 544/402, 280, 281, 350, 544/360, 368; 514/255, 248, 249

[56] References Cited

FOREIGN PATENT DOCUMENTS 0100257 8/1984 European Pat. Off. .
2533 3/1964 France .

OTHER PUBLICATIONS

Henry, Chem. Abst., vol. 66 (1967), 37889k.
Duncan et al, Chem. Abst., vol. 70(1969), 47401s.
Hasegawa et al, Chem. Abst., vol. 77(1972), 48507n.
Roch et al, Chem. Abst., vol. 89(1978), 6322r.
Hino et al, Chem. Abst., vol. 94(1981), 30538q.
Schoofs et al, Chem. Abst., 101-6860f (1984).
Barreau et al, Chem. Abst. 107-175903b (1987).

Chemical Abstracts, vol. 77, 1972, pp. 496-497-No. 48507n.
Chemical and Pharmaceutical Bulletin, vol. 28, No. 9, 1980, pp. 2618-2622.

Primary Examiner—Donald G. Daus
Assistant Examiner—Cecilia Shen
Attorney, Agent, or Firm—Stevens, Davis, Miller & Mosher

[57] ABSTRACT

Compounds of formula (I) in which the broken line forms a phenyl, naphthyl, pyridyl, indolizine, pyrrolo[1,2-a]pyrazine, pyrrolo[1,2-a]pyrimidine or pyrrolo[1,2-c]pyrimidine ring-system, R=H, halogen, OH, alkyl, alkyloxy or alkylthio, R'=H, halogen, alkyl, alkyloxy, alkylthio, CN or CF$_3$, n and p=1, 2 or 3, the alkyl radicals having 1 to 4 C in a straight or branched chain.

These products are useful as neuroleptics.

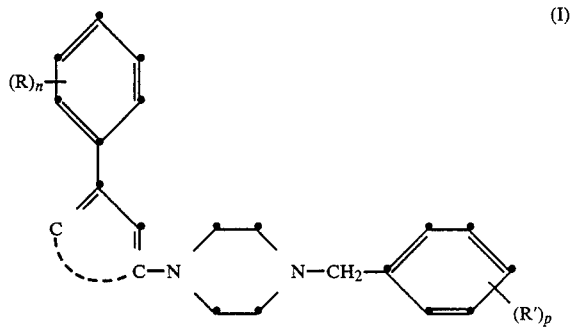

12 Claims, No Drawings

4-BENZYLPIPERAZINES USEFUL AS NEUROLEPTICS

The present invention provides compounds of general formula I:

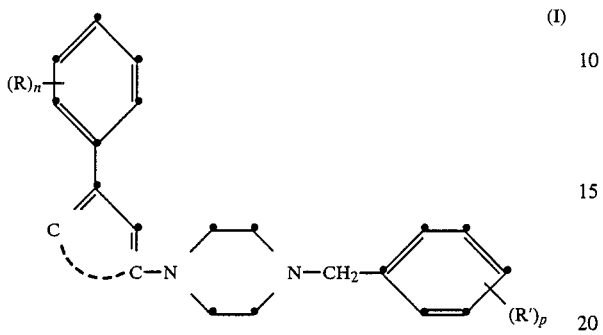

in which the broken line forms, with the chain of four carbon atoms to which it is attached, a phenyl, naphthyl, pyridine, indolizine, pyrrolo[1,2-a]pyrazine, pyrrolo[1,2-a]pyrimidine or pyrrolo[1,2-c]pyrimidine ring-system, R is a hydrogen or halogen ato or a hydroxy, alkyl, alkyloxy or alkylthio radical, R' is a hydrogen or halogen atom or an alkyl, alkyloxy, alkylthio, cyano or trifluoromethyl radical, and n and p, which may be the same or different, are each 1, 2 or 3, and in which an alkyl radical or alkyl moiety contains 1 to 4 carbon atoms in a straight or branched chain, and pharmaceutically acceptable acid addition salts thereof.

The products of general formula (I) in which the broken line forms, with the chain of four carbon atoms to which it is attached, a phenyl or naphthyl ring-system may be prepared by the action of a derivative of general formula II:

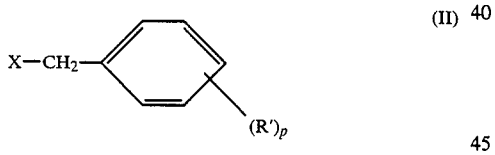

in which R' and p arre defined as above and X is a halogen atom such as a chlorine or bromine atom or an activated ester residue such as a mesyloxy or tosyloxy radical, on a product of general formula III:

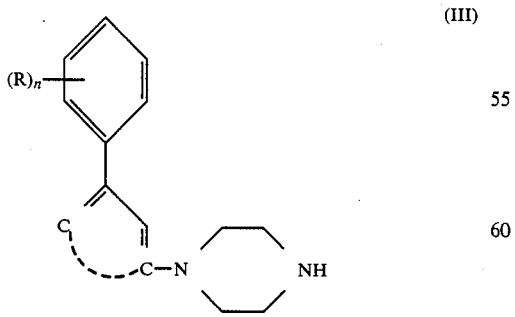

in which the broken line forms, with the chain of four carbon atoms to which it is attached, a phenyl or naphthyl ring-system and the other symbols are defined as above.

The reaction is generally performed in an organic solvent such as acetonitrile or a chlorinated solvent such as chloroform, in the presence of an acceptor for acid such as a carbonate, e.g. potassium carbonate, or 4-dimethylaminopyridine, at a temperature between 20° C. and the refluxing temperature of the reaction mixture.

The products of general formula (III) may be prepared by the action of bis(2-chloroethyl)amine on an amine of general formula IV:

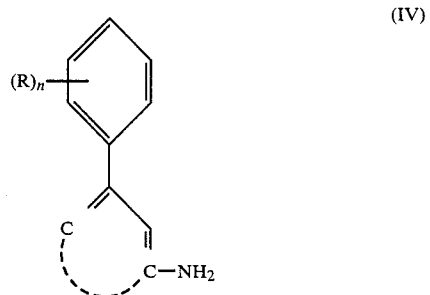

in which the broken forms, with the chain of four carbon atoms to which it is attached, a phenyl or naphthyl ring-system and the other symbols are defined as above.

The reaction is generally performed in a solvent of high boiling point such as 1,2,4-trichlorobenzene, at a temperature between 150° C. and the refluxing temperature of the reaction mixture.

The products of general formula (IV) may be prepared by application or adaptation of the methods described in the literature.

The products of general formula (I) in which the broken line forms, with the chain of four carbon atoms to which it is attached, a pyridine ring may be prepared by the action of a piperazine of general formula V:

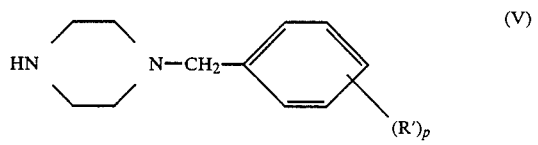

in which R' and p are defined as above, on a product of general formula VI:

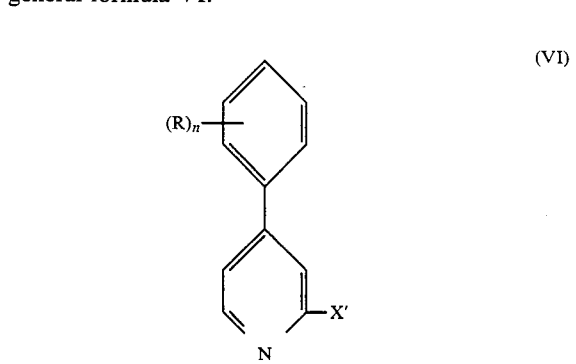

in which R and n are defined as above and X' is a halogen atom such as a chlorine or bromine atom.

The reaction is generally performed in an organic solvent of high boiling point such as 1,2,4-trichlorobenzene, at a temperature between 80° C. and the refluxing temperature of the reaction mixture.

The products of general formula (VI) may be prepared by adaptation of the methods known in the literature for obtaining a 2-halopyridine, e.g. by the action of phosphoryl chloride on a product of general formula VII:

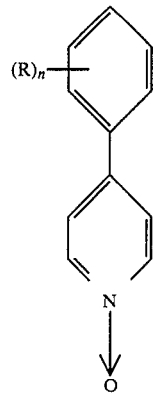

(VII)

in which R and n are defined as above.

The reaction is generally performed by heating in an autoclave at a temperature in the region of 190° C.

The products of general formula (VII) may be obtained by application or adaptation of the methods known and described in the literature.

The products of general formula (I) in which the broken line forms, with the chain of four carbon atoms to which it is attached, an indolizine, pyrrolo[1,2-a]pyrazine, pyrrolo[1,2-a]pyrimidine or pyrrolo[1,2-c]pyrimidine ring-system may be prepared by the action of a piperazine of general formula (V) defined as above on an aldehyde of general formula VIII:

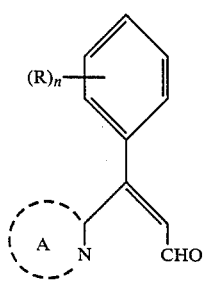

(VIII)

in which R and n are defined as above and A is a 2-pyridyl, pyrazinyl, 2-pyrimidinyl or 4-pyrimidinyl radical.

The reaction is generally performed in an organic solvent such as an ether, e.g. tetrahydrofuran or dioxane, at a temperature between 50° C. and the refluxing temperature of the reaction mixture.

The products of general formula (VIII) in which A is a 2-pyridyl or pyrazinyl radical may be prepared by the action of diethyl 1-(2-cyclohexylaminovinyl)phosphonate on a product of general formula IX:

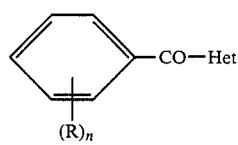

(IX)

in which R and n are defined as above and Het is a 2-pyridyl or pyrazinyl radical.

The reaction is generally performed in the presence of a base such as a hydride, e.g. sodium hydride, in an organic solvent such as an ether, e.g. tetrahydrofuran, at a temperature between 25° C. and the refluxing temperature of the reaction mixture.

The products of general formula (IX) may be prepared by application or adaptation of known methods.

The products of general formula (VIII) in which A is a pyrimidinyl radical may be prepared by oxidation of the corresponding alcohol of general formula X:

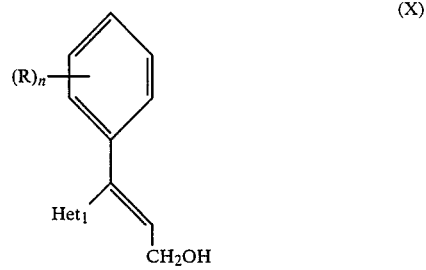

(X)

in which R and n are defined as above and $Het_1$ is a 2- or 4-pyrimidinyl radical.

The reaction is generally performed by any known means for oxidizing an alcohol to aldehyde without affecting the remainder of the molecule, e.g. by means of manganese dioxide in a solvent such as dioxane, at a temperature in the region of 20° C.

The alcohols of general formula (X) may be prepared by reduction of the esters of general formula XI:

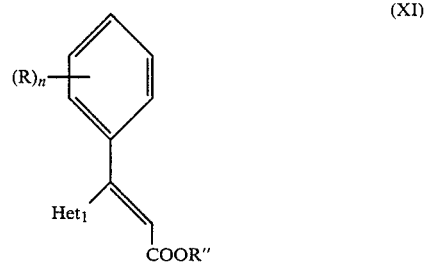

(XI)

in which $Het_1$ is a $Het_1$ is a 2- or 4-pyrimidinyl radical, R" is a straight- or branched-chain alkyl radical containing 1 to 4 carbon atoms and R and n are defined as above.

The reaction is performed by any known method for reducing an ester to alcohol, e.g. by means of diisobutylaluminium hydride in a solvent such as toluene, at a temperature in the region of −78° C.

The esters of general formula (XI) may be prepared by adaptation of the method described by E. C. Taylor and S. F. Martin, J. Am. Chem. Soc. 96, 8095 (1974).

The compounds of general formula (I) may be purified by known methods, e.g. by crystallization, chromatography, successive extractions in acidic and basic medium or formation of salts and recrystallization of the latter.

The compounds of general formula (I) may be converted to addition salts with acids by the action of an acid in an organic solvent such as an alcohol, a ketone, an ether or a chlorinated solvent. The salt formed precipitates, where appropriate after concentration of its solution; it may be separed by filtration or decantation.

The compounds of general formula (I) and their pharmaceutically acceptable salts have advantageous pharmacological properties which make them useful as antipsychotics or neuroleptics. They have been shown to be active in mice at doses of between 0.5 and 20 mg/kg orally in the test of antagonism of apomorphine-induced rearing according to the technique of P. Protais et al., Psychopharmacology, 50, 1 (1976).

The compounds of general formula (I) possess low toxicity. Their oral $LD_{50}$ is between 100 and 900 mg/kg in mice.

Of special value are the compounds of general formula (I) in which the broken line forms, with the chain of four carbon atoms to which it is attached, an aromatic ring-system chosen from phenyl, naphthyl, pyridine, indolizine, pyrrolo[1,2-a]pyrazine or pyrrolo[1,2-a]pyrimidine ring-systems, R is a hydrogen atom, R' is a hydrogen atom or an alkyl radical and n and p are each 1, and in which an alkyl radical or alkyl moiety contains 1 to 4 carbon atoms in a straight or branched chain, and pharmaceutically acceptable acid or base addition salts thereof.

The following products are of special value:
3-[4-(4-methylbenzyl)-1-piperazinyl]biphenyl
1-[4-(4-methylbenzyl)-1-piperazinyl]-3-phenylnaphthalene
2-[4-(4-methylbenzyl)-1-piperazinyl]-4-phenylpyridine
3-[4-(4-methylbenzyl)-1-piperazinyl]-1-phenylindolizine
3-[4-(4-methylbenzyl)-1-piperazinyl]-1-phenylpyrrolo[1,2-a]pyrazine
3-[4-(4-methylbenzyl)-1-piperazinyl]-1-phenylpyrrolo[1,2-a]pyrimidine As examples of pharmaceutically acceptable salts, there may be mentioned the addition salts with inorganic acids (such as hydrochlorides, sulphates, nitrates, phosphates) or organic acids [such as acetates, propionates, succinates, benzoates, fumarates, maleates, methanesulphonates, isethionates, theophyllineacetates, salicylates, phenolphthalinates, methylenebis($\beta$-oxynaphthoates)] or substitution derivatives of them compounds.

The examles which follow illustrate the invention.

EXAMPLE 1

To a solution of 3-[1-piperazinyl]biphenyl (11.9 g) in aceonitrile (200 cc), there is added potassium carbonate (6.9 g) and then, in the course of 20 minutes, a solution of $\alpha$-chloro-p-xylene (8 g) in acetonitrile (50 cc), at a temperature in the region of 20° C., and stirring is continued for 16 hours. The insoluble material which has formed is separated by filtration. The solution obtained is concentrated under reduced pressure (20 mm Hg; 2.7 kPa) at 40° C. The residue is dissolved in methylene chloride (30 cc) and the solution poured onto silica (1 kg) contained in a column 8 cm in diameter. Elution is performed with a mixture (3 liters) of methylene chloride and methanol (97.5:2.5 by volume) and the corresponding eluate is concentrated to dryness under reduced pressure (20 mm Hg; 2.7 kPa) at 50° C. The residue obtained is dissolved in acetone (600 cc). The solution is cooled to a temperature in the region of 5° C., 2.5N ethereal hydrogen chloride (40 cc) is added and stirring is maintained for approximately 1 hour. The precipitate formed is separated by filtration and washed with acetone (2×40 cc). 3-[4-(4-Methylbenzyl)-1-piperazinyl]biphenyl dihydrochloride (17.3 g), m.p. 241° C., is thereby obtained.

3-(1-Piperazinyl)biphenyl may be prepared in the following manner: A solution of 3-aminobiphenyl (24.3 g) and bis(2-chloroethyl)amine (29.8 g) in 1,2,4-trichlorobenzene (60 cc) is heated for 6 hours at 170° C. After the mixture is cooled to a temperature in the region of 20° C., isopropyl ether (400 cc) is added. The precipitate formed is separated by filtration, washed with isopropyl ether (3×50 cc) and the dissolved in ethyl acetate (500 cc). 5N aqueous sodium hydroxide solution (44 cc) is added, followed by distilled water (200 cc). The organic phase is decanted and the aqueous phase washed with ethyl acetate (2×100 cc). The organic extracts are combined, dried over anhydrous magnesium sulphate, filtered and concentrated to dryness under reduced pressure (20 mm Hg; 2.7 kPa) at 40° C. The residue obtained is dissolved in methylene chloride (30 cc) and the solution poured onto silica (1 kg) contained in a column 8 cm in diameter. Elution is performed with a mixture (3 liters) of methylene chloride and methanol (90:10 by volume) and the corresponding eluate is concentrated to dryness under reduced pressure (20 mm Hg; 2.7 kPa) at 50° C. 3-(1-Piperazinyl9-biphenyl (18.8 g) is thereby obtained in the form of a yellowish pasty solid, which is used without further purification in the subsequent syntheses.

3-Aminobiphenyl may be prepared according to the method described by H. H. Bosshard and H. Zollinger, Helv. Chim. Acta 44, 1985 (1961).

EXAMPLE 2

To a stirred solution of 3-phenyl-1-(1-piperazinyl)-naphthalene (17.9 g) in acetonitrile (280 cc), there is added potassium carbonate (8.6 g) and then, in the course of 20 minutes, a solution of $\alpha$-chloro-p-xylene (8.7 g) in acetonitrile (50 cc), at a temperature in the region of 20° C., and stirring is continued for 16 hours. The insoluble material which is formed is separated by filtration. The solution obtained is evaporated under reduced pressure (20 mm Hg; 2.7 kPa) at 40° C. The residue is dissolved in methylene chloride (35 cc) and the solution poured onto silica (1 kg) contained in a column 7.5 cm in diameter. Elution is performed with a mixture (3 liters) of methylene chloride and methanol (99:1 by volume) and the corresponding eluate is concentrated to dryness under reduced pressure (20 mm Hg; 2.7 kPa) at 50° C. The residue obtained is dissolved in acetone (250 cc). The solution is cooled to a temperature in the region of 5° C., a 2.5N solution (52 cc) of anhydrous hydrochloric acid in ethyl ether is added and stirring is maintained for approximately 4 hours. The precipitates formed is separated by filtration and washed with ethyl ether ether (3×25 cc). 1-[4-(4-Methylbenzyl)-1-piperazinyl]-3-phenylnaphthalene dihydrochloride (19 g), m.p. 252° C., is thereby obtained.

3-Phenyl-1-(1-piperazinyl)naphthalene may be prepared in the following manner: bis(2-chloroethyl)amine (43.3 g) dissolved in methanol (100 cc) is added to a solution of 1-amino-3-phenylnaphthalene (21.5 g) in methanol (100 cc). The mixture is concentrated to dryness under reduced pressure (20 mm Hg; 2.7 kPa) at 50°

C. 1,2,4-trichlorobenzene (200 cc) is added to the residue and the mixture is stirred at 170° C. for 13 hours. After the mixture is cooled to a temperature in the region of 20° C., isopropyl ether (300 cc) is added. The precipitates formed is separated by filtration, washed with isopropyl ether (3×50 cc) and then dissolved in ethyl acetate (5 liters). 5N aqueous sodium hydroxide solution (200 cc) is added, followed by distilled water (500 cc). The organic solution is decanted and the aqueous and the aqueous phase washed with ethyl acetate (1 liter). The organic extracts are combined, dried over anhydrous magnesium sulphate, filtered and concentrated to dryness under reduced pressure (20 mm Hg; 2.7 kPa) at 40° C. The oil obtained is dissolved in methylene chloride (40 cc) and the solution obtained is poured onto silica (600 g) contained in a column 7 cm in diameter. Elution is performed with a mixture (3.5 liters) of methylene chloride and methanol (90:10 by volume) and the corresponding eluate is concentrated to dryness under reduced pressure (20 mm Hg; 2.7 kPa) at 50° C. 3-Phenyl-1-(1-piperazinyl)naphthalene (16.9 g) is thereby obtained in the form of a very viscous brown oil, which is used without further purification in the subsequent syntheses.

1-Amino-3-phenylnaphthalene may be prepared in the following manner: a stream of gaseous hydrochloric acid is bubbled for 2 hours at a temperature in the region of 25° C. through a solution of 3-phenyl-1-tetralone oxime (51.2 g), acetic acid (215 cc) and acetic anhydride (43 cc), and stirring is maintained for 16 hours. The precipitate formed is separated by filtration, washed 3 times with ethyl ether (90 cc in total) and then taken up with methylene chloride (350 cc). 5N aqueous sodium hydroxide solution (66 cc) is added to the mixture, followed by distilled water (100 cc). The organic phase is decanted and the aqueous phase washed with methylene chloride (100 cc.) The organic extracts are combined, dried over anhydrous magnesium sulphate, filtered and concentrated to dryness under reduced pressure (20 mm Hg; 2.7 kPa) at 40° C. The residue obtained is dissolved in methylene chloride (40 cc) and the solution poured onto silica (1 kg) contained in a column 7 cm in diameter. Elution is performed with methylene chloride (3.5 liters) and the corresponding eluate is concentrated to dryness under reduced pressure (20 mm Hg; 2.7 kPa) at 40° C. 1-Amino-3-phenylnaphthalene (12 g), m.p. approximately 103° C., is thereby obtained.

3-Phenyl-1-tetralone oxime may be prepared in the following manner: A solution of 3-phenyl-1-tetralone (160 g) and hydroxylamine hydrochloride (98 g) in pyridine (750 cc) and ethanol (1500 cc) is heated for 3 hours at a temperature in the region of 80° C. After being cooled to a temperature in the region of 20° C., the solution is concentrated to dryness under reduced pressure (20 mm Hg; 2.7 kPa) at 60° C. The residue is taken up with distilled water (1.5 liters) and the mixture is heated for 1 hour at a temperature in the region of 80° C. After the mixture is cooled to 20° C., the precipitate formed is filtered off and washed with distilled water (2×100 cc). 3-Phenyl-1-tetralone oxime (85.6 g), m.p. 195° C., is thereby obtained.

3-Phenyl-1-tetralone may be prepared according to the method described by J. P. Quillet, A. Duperrier and J. Dreux, Bull. Soc. Chim. France, 1, 255 (1967).

EXAMPLE 3

A solution of 2-chloro-4-phenylpyridine (11.4 g) and 4-(4-methylbenzyl)piperazine (11.4 g) in 1,2,4-trichlorobenzene (40 cc) is heated for 5 hours at 170° C. After the mixture is cooled to a temperature in the region of 20° C., isopropyl ether (200 cc) is added. The precipitate formed is separated by filtration, washed with isopropyl ether (50 cc) and then dissolved in ethyl acetate (250 cc). 5N aqueous sodium hydroxide solution (16 cc) is added, followed by distilled water (100 cc). The organic solution is decanted and the aqueous phase washed with ethyl acetate (2×50 cc). The organic extracts are combined, dried over anhydrous magnesium sulphate, filtered and evaporated to dryness under reduced pressure (20 mm Hg; 2.7 kPa) at 40° C. The residue is dissolved in 2-propanol (75 cc); decolorizing charcoal (0.5 g) is added and the mixture is heated to 100° C. for 30 minutes, filtered on diatomaceous earth and cooled to 10° C. for 1 hour. The precipitate formed is separated by filtration and washed with 2-propanol (2×10 cc). 2-[4-(4-Methylbenzyl)-1-piperazinyl]-4-phenylpyridine (8 g), m.p. 103° C., is thereby obtained.

2-Chloro-4-phenylpyridine may be prepared in the following manner: A mixture of 4-phenylpyridine N-oxide hydrochloride (26 g) and phosphoryl chloride (75 cc) is heated for 16 hours at 190° C. in an autoclave internally clad with a tantalum lining. After the mixture is cooled to a temperature in the region of 20° C., the excess phosphoryl chloride is removed by distillation under reduced pressure (20 mm Hg; 2.7 kPa) at 50° C. The residue is taken up with ice-cold water (100 cc) and 5N aqueous sodium hydroxide solution (40 cc). The aqueous solution is washed with ethyl acetate (1×500 cc followed by 2×250 cc). The organic extracts are combined, dried over anhydrous magnesium sulphate, filtered and concentrated to dryness under reduced pressure (20 mm Hg; 2.7 kPa) at 40° C. The residue obtained is dissolved in methylene chloride (40 cc) and the solution poured onto silica (500 g) contained in a column 6 cm in diameter. Elution is performed with methylene chloride (3 liters) and the eluate is evaporated to dryness under reduced pressure (20 mm Hg; 2.7 kPa) at 40° C. 2-Chloro-4-phenylpyridine (18.1 g), m.p. 70°–72° C., is thereby obtained.

4-Phenylpyridine N-oxide may be prepared according to the method described by K. Kawematsu, M. Takeda, A. E. Jacobson and E. L. May, J. Med. Chem., 12, 405 (1969).

EXAMPLE 4

A solution of 1-(4-methylbenzyl)piperazine (14 g) in tetrahydrofuran (30 cc) is added in the course of 15 minutes at a temperature in the region of 20° C. to a stirred solution of 3-phenyl-3-(2-pyridyl)propenal (5.4 g) in tetrahydrofuran (150 cc), and the mixture is left with stirring for 8 hours at a temperature in the region of 66° C. After the solution is cooled to a temperature in the region of 20° C., the reaction mixture is evaporated to dryness under reduced pressure (20 mm Hg; 2.7 kPa) at 40° C. The residue obtained is dissolved in ethyl ether (50 cc) and the solution obtained poured onto silica (400 g) contained in a column 4.7 cm in diameter. Elution is performed with a mixture (300 cc) of ethyl ether and petroleum ether (40°–65° C.) (80:20 by volume) and the corresponding eluate is concentrated to dryness under reduced pressure (20 mm Hg; 2.7 kPa) at 40° C. The oil obtained is dissolved in boiling ethyl ether (200 cc). A boiling 2.5N solution (3 cc) of hydrochloric acid in ethyl alcohol is added. After the mixture is cooled to a temperature in the region of 20° C, the precipitate formed is separated by filtration and then recrystallized in boiling ethyl alcohol (400 cc). 3-[4-(4-Methylbenzyl)-1-piperazinyl]-1-phenylindolizine hydrochloride (3.1 g), m.p. 210° C. with decomposition, is thereby obtained.

3-Phenyl-3-(2-pyridyl)propenal may be prepared in the following manner: A solution of diethyl 1-(2-cyclohexylaminovinyl)phosphonate (17 g) in dry tetrahydrofuran (300 cc) is added in the course of 15 minutes at a temperature in the region of 20° C. to a suspension, stirred under an atmosphere of nitrogen, of sodium hydride (3 g) (washed beforehand with dry ethyl ether, 2×20 cc) and dry tetrahydrofuran (40 cc), and the mixture is left with stirring for 2 hours at a temperature in the region of 45° C. After the solution is cooled to a temperature in the region of 20° C., 2-benzoylpyridine (8 g) dissolved in dry tetrahydrofuran (100 cc) is added and the mixture is left with stirring for 5 hours at a temperature in the region of 45° C. After the solution is cooled to a temperature in the region of 20° C., distilled water (10 cc) is added and the tetrahydrofuran is evaporated off under reduced pressure (20 mm Hg; 2.7 kPa) at 40° C. To the residue obtained, sodium acetate (20 g) dissolved in a mixture of acetic acid (12 g) and distilled water (200 cc) is added, followed by ethyl ether (400 cc), and the mixture is stirred for 20 minutes. The ether phase is decanted and the aqueous phase extracted with ethyl ether (2×200 cc). The organic phases are combined, washed with saturated aqueous sodium bicarbonate solution (100 cc) and then with saturated aqueous sodium chloride solution (100 cc), dried over magnesium sulphate, filtered and evaporated under reduced pressure (20 mm Hg; 2.7 kPa) at 40° C. The residue is dissolved in ethyl ether (50 cc) and the solution poured onto silica (800 g) contained in a column 6.5 cm in diameter. Elution is performed first with a mixture (500 cc) of ethyl ether and petroleum ether (40°–65° C.) (35–65 by volume); the corresponding eluates are discarded. Elution is then performed with a mixture (500 cc) of ethyl ether and petroleum ether (40°–65° C.) (50:50 by volume) and the corresponding eluate is concentrated to dryness under reduced pressure (20 mm H; 2.7 kPa) at 40° C. 3-Phenyl-3-(2-pyridyl)propenal (5.4 g) is thereby obtained, and this is used in the crude state in the subsequent syntheses.

Diethyl 1-(2-cyclohexylaminovinyl)phosphonate may be prepared according to the method described by V. Nagata and Y. Hayase, J. Chem. Soc. (C), 460 (1969).

EXAMPLE 5

A solution of 1-(4-methylbenzyl)piperazine (9.5 g) in tetrahydrofuran (50 cc) is added in the course of 10 minutes at a temperature in the region of 20° C. to a stirred solution of 3-phenyl-3-pyrazinylpropenal (1 g) in tetrahydrofuran (50 cc), and the mixture is left with stirring for 3 hours at a temperature in the region of 66° C. After the solution is cooled to a temperature in the region of 20° C., the reaction mixture is concentrated to dryness under reduced pressure (20 mm Hg; 2.7 kPa) at 40° C. A residue is obtained which is dissolved in methylene chloride (10 cc). The solution obtained is poured onto silica (200 g) contained in a column 3.5 cm in diameter. Elution is performed with a mixture (500 cc) of methylene chloride and methanol (99.5:0.5 by volume) and the corresponding eluate is evaporated to dryness under reduced pressure (20 mm Hg; 2.7 kPa) at 40° C. The oil obtained is dissolved in boiling methyl ethyl ketone (20 cc). A solution of oxalic acid (0.25 g) in boiling methyl ethyl ketone (20 cc) is added. After the mixture is cooled to a temperature in the region of 20° C., the precipitate formed is separated by filtration and then recrystallized in boiling isopropyl alcohol (80 cc). 3-[4-(4-Methylbenzyl)-1-piperazinyl]-1-phenylpyrrolo[1,2-a]pyrazine oxalate (0.4 g), m.p. 128° C., is thereby obtained.

3-Phenyl-3-pyrazinylpropenal may be prepared in the following manner: A solution of diethyl 1-(2-cyclohexylaminovinyl)phosphonate (44.3 g) in dry tetrahydrofuran (300 cc) is added in the course of 30 minutes at a temperature of 20° C. to a suspension, stirred under an atmosphere of nitrogen, of sodium hydride (4.1 g) washed beforehand with dry ethyl ether (2×30 cc) and dry tetrahydrofuran (50 cc), and the mixture is left with stirring for 2 hours at a temperature in the region of 45° C. After the solution is cooled to a temperature in the region of 20° C., benzoylpyrazine (15.6 g) dissolved in dry tetrahydrofuran (200 cc) is added and the mixture is left with stirring for 5 hours at a temperature in the region of 45° C. After the solution is cooled to a temperature in the region of 20° C., distilled water (15 cc) is added and the mixture is evaporated to dryness under reduced pressure (20 mm Hg; 2.7 kPa) at 40° C. A residue is obtained which is dissolved in methylene chloride (150 cc). The solution is poured onto silica (700 g) contained in a column 8 cm in diameter. Elution is performed with methylene chloride (1200 cc); the corresponding eluate is concentrated to dryness under reduced pressure (20 mm Hg; 2.7 kPa) at 40° C. 3-Phenyl-3-pyrazinylpropenal (1 g) is thereby obtained in the form of a brown oil. $R_f$=0.58 [thin layer chromatography on silica gel; solvent:methylene chloride/methanol (95:5)].

Benzoyl pyrazine may be prepared in the following manner: A solution of bromobenzene (32.5 g) in ethyl ether (350 cc) is added in the course of 1 hour, while stirring under an atmosphere of nitrogen, at a temperature in the region of 20° C., to magnesium turnings (4.1 g), and the mixture is left with stirring for a further 1 hour at a temperature in the region of 35° C. and then for 15 hours at a temperature in the region of 20° C. Cyanopyrazine (17.4 g) in ethyl ether (150 cc) is then added and the mixture is left with stirring for 2 and a half hours. Distilled water (250 cc) is then added, the mixture is left with stirring for 1 and a half hours at a temperature in the region of 5° C., saturated aqueous ammonium chloride solution (150 cc) is added and the mixture is left with stirring for 1 hour. The ether phase is decanted and the aqueous phase extracted with ethyl ether (3×100 cc). The organic phases are combined, washed with distilled water (20 cc), dried over magnesium sulphate and filtered. The solvent is evaporated off under reduced pressure (20 mm Hg; 2.7 kPa) at 30° C. The residue obtained is dissolved in cyclohexane (100 cc) and the solution obtained is poured onto silica (600 g) contained in a column 5 cm in diameter. Elution is performed with a mixture (1 liter) of cyclohexane and ethyl acetate (95:5 by volume); the corresponding eluates are discarded. Elution is then performed with the same mixture (4 liters) and the corresponding eluate is evaporated to dryness under reduced pressure (20 mm Hg; 2.7 kPa) at 40° C. Benzoylpyrazine (12.5 g) is thereby obtained in the form of an orange oil. $R_f$=0.35 [thin layer chromatography on silica gel; solvent: cyclohexane/ethyl acetate (60:40)].

Cyanopyrazine may be prepared according to the method described by M. Robba, Ann. de Chimie, 13 (B) 379 (1960).

Diethyl 1-(2-cyclohexylaminovinyl)phosphonate may be prepared according to the method described by V. Nagata and Y. Hayase, J. Chem. Soc. (C) 460 (1969).

EXAMPLE 6

A solution of 3-phenyl-3-(2-pyrimidinyl)propenal (1.25 g) in tetrahydrofuran (125 cc) is added to 4-(4-methylbenzyl)piperazine (11.2 g). The solution is stirred and heated to a temperature in the region of 65° C. for 3 hours. After being coiled to a temperature in the region of 20° C., the reaction mixture is concentrated to dryness under reduced pressure (20 mm Hg; 2.7 kPa) at 40° C. The residue obtained is dissolved in ethyl acetate (10 cc) and the solution obtained is poured onto silica (25 g) contained in a column 1.5 cm in diameter. Elution is performed with a mixture (750 cc) of ethyl acetate and cyclohexane (50:50 by volume); the corresponding eluates are discarded. Elution is then performed with the same mixture (300 cc) and the corresponding eluate is concentrated to dryness under reduced pressure (20 mm Hg; 2.7 kPa) at 40° C. The oil obtained is dissolved in methyl ethyl ketone (20 cc). Oxalic acid (120 mg) dissolved in methyl ethyl ketone (20 cc) is added and the mixture is stirred for approximately 15 minutes at a temperature in the region of 20° C. The precipitate formed is separated by filtration and then recrystallized in boiling isopropyl alcohol (50 cc). 3-[4-(4-Methylbenzyl)-1-piperazinyl]-1-phenylpyrrolo[1,2-a]pyrimidine oxalate (300 mg), m.p. 205° C., is thereby obtained.

3-Phenyl-3-(2-pyrimidinyl)propenal may be prepared in the following manner: A suspension of 3-phenyl-3-(2-pyrimidinyl)-2-propen-1-ol (1.5 g) and manganese dioxide (6.25 g) in dioxane is stirred vigorously at a temperature in the region of 20° C. for approximately 16 hours. The precipitate is then separated by filtration and the filtrate evaporated to dryness under reduced pressure (20 mm Hg; 2.7 kPa) at 60° C. 3-Phenyl-3-(2-pyrimidinyl)propenal (1.25 g) is thereby obtained in the form of a yellow oil. $R_f = 0.78$ (thin layer chromatography on silica gel; solvent: ethyl acetate).

3-Phenyl-3-(2-pyrimidinyl)-2-propen-1-ol may be prepared in the following manner: A 1.2M solution (15 cc) of diisobutylaluminium hydride in toluene is added in the course of approximately 15 minutes to a solution, maintained under an atmosphere of nitrogen at a temperature in the region of −78° C., of butyl 3-phenyl-3-(2-pyrimidinyl)acrylate (2.5 g) in dry toluene (150 cc), and stirring is continued for 1 hour at a temperature in the region of −78° C. The temperature is then allowed to rise to approximately 0° C. during approximately 3 hours, then saturated aqueous ammonium chloride solution (150 cc) is added, the mixture is decanted and the organic phase separated. The aqueous phase is extracted twice with methylene chloride (150 cc in total). The organic phases are combined and dried over magnesium sulphate, filtered and concentrated to dryness under reduced pressure (20 mm Hg; 2.7 kPa) at 50° C. 3-Phenyl-3-(2-pyrimidinyl)-2-propen-1-ol (1.5 g) is thereby obtained in the form of a yellow oil. $R_f = 0.57$ (thin layer chromatography on silica gel; solvent: ethyl acetate).

Butyl 3-phenyl-3-(2-pyrimidinyl)acrylate may be prepared in the following manner: A 1.6M solution (20 cc) of n-butyllithium in hexane is added in the course of approximately 20 minutes to a suspension, stirred under an atmosphere of nitrogen at a temperature in the region of −30° C., of tributylbenzenephosphonium bromide (12.2 g) in dry 1,2-dimethoxyethane (140 cc). The suspension is allowed to rise to a temperature in the region of 20° C. in the course of approximately 1 hour, and stirring is continued for a further 1 hour at this same temperature. 2-Chloropyrimidine (1.75 g) suspended in dry dimethoxyethane (40 cc) is then added and the mixture is heated for approximately 5 hours to a temperature in the region of 70° C. The temperature of the solution is then lowered to approximately 20° C. A 1.6M solution (10 cc) of n-butyllithium in hexane is then added and the suspension is heated again to approximately 70° C. for 3 hours. After the solution is cooled to a temperature in the region of 20° C., the reaction mixture is added in the course of 30 minutes to a solution of butyl glyoxylate (3.8 g) in 1,2-dimethoxyethane (20 cc) and the suspension is heated for 24 hours to a temperature in the region of 70° C. After the solution is cooled to a temperature in the region of 20° C., the suspension obtained is filtered. The filtrate is diluted with ethyl ether (200 cc) and washed with distilled water (200 cc). The mixture is decanted, the organic phase is separated and aqueous phase extracted with ethyl ether (100 cc). The organic phases are combined, dried over magnesium sulphate, filtered and concentrated to dryness under reduced pressure (20 mm Hg; 2.7 kPa) at 30° C. The residue obtained is dissolved in methylene chloride (30 cc) and the solution poured onto silica (500 g) contained in a column 5 cm in diameter. Elution is performed with a mixture (1000 cc) of methylene chloride and cyclohexane (50:50 by volume); the corresponding eluates are discarded. Elution is then performed with the same mixture (500 cc) and the corresponding eluate is evaporated to dryness under reduced pressure (20 mm Hg; 2.7 kPa) at 40° C. Butyl 3-phenyl-3-(2-pyrimidinyl)acrylate (2.5 g) is thereby obtained in the form of a yellow oil. $R_f = 0.75$ (thin layer chromatography on silica gel; solvent: ethyl acetate).

The present invention also relates to pharmaceutical compositions comprising a compound of general formula (I), in free form or in the form of a pharmaceutically acceptable acid addition salt. The composition may optionally also comprise any other pharmaceutically compatible product which may be inert or physiologically active. The pharmaceutical compositions may be used orally or parenterally.

As solid compositions for oral administration, tablets, pills, powders (in particular, in gelatin capsules or wafer capsules) or granules may be used. In these compositions, a compound according to the invention is mixed with one or more inert diluents such as starch, cellulose, sucrose, lactose or silica. These compositions can also include substances other than diluents, e.g. one or more lubricants such as magnesium stearate or talc, a colouring, a coating (dragees) or a lacquer.

As liquid compositions for oral administration, solutions, suspensions, emulsions, syrups and elixirs which are pharmaceutically acceptable may be used, containing inert diluents such as water, ethanol, glycerol, vegetable oils or liquid paraffin. These compositions can also include substances other than diluents, e.g. wetting, sweetening, thickening, flavouring or stabilizing products.

The sterile compositions for parenteral administration is preferably an aqueous or non-aqueous solution, or suspension or emulsion. As a solvent or vehicle, water, propylene glycol, a polyethylene glycol, vegetable oils, especially olive oil, injectable organic esters, e.g. ethyl oleate, or other suitable organic solvents may be employed. These compositions can also contain adjuvants, especially wetting agents, tonicity-regulating agents, emulsifiers, dispersants and stabilizers. The sterilization can be carried out in several ways, e.g. by aseptic filtration, by incorporating sterilizing agents in the composition, by irradiation or by heating. They can also be prepared in the form of sterile solid compositions which can be dissolved at the time of use in an injectable sterile medium.

In human therapy, the compounds are especially useful in the treatment of disorders of the mind, and more especially psychoses such as schizophrenia or delirium states. The dosages depend on the effect sought and the period of treatment; they are generally between 25 and 250 mg per day orally for an adult, taken in one or more doses.

In general, the medical practioner will determine the dosage which he judges to be most appropriate in accordance with the age, weight and all other factors specific to the subject to be treated.

The examples which follow illustrate compositions according to the invention.

EXAMPLE A

Tablets containing a 25-mg dose of active product and having the following composition are prepared according to the customary technique:

| | |
|---|---|
| 3-[4-(4-methylbenzyl)-1-piperazinyl]biphenyl dihydrochloride | 30.25 mg |
| starch | 60 mg |
| lactose | 50 mg |
| magnesium stearate | 2 mg |

EXAMPLE B

An injectable solution is prepared containing 25 mg of active product and having the following composition:

| | |
|---|---|
| 2-[4-(4-methylbenzyl)-1-piperazinyl]-4-phenylpyridine | 25 mg |
| 0.1 N aqueous hydrochloric acid solution | 2.18 cc |
| injectable solution | qs 10 cc |

We claim:

1. A compound of the formula I:

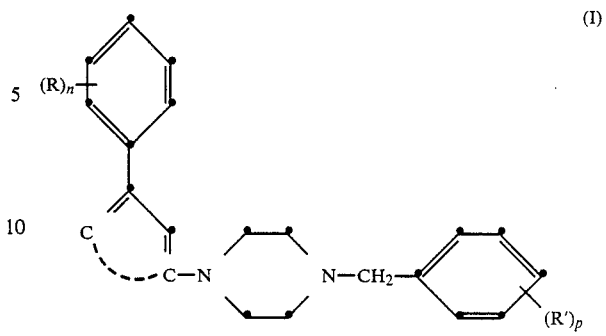

in which the broken line forms, with the chain of four carbon atoms to which it is attached, a phenyl, naphthyl, pyridine, indolizine, pyrrolo[1,2-a]pyrazine, pyrrolo[1,2-a]pyrimidine or pyrrolo[1,2-c]pyrimidine ring-system, R is a hydrogen or halogen atom or a hydroxy, alkyl, alkyloxy or alkylthio radical, R' is a hydrogen or halogen atom or an alkyl, alkyloxy, alkylthio, cyano or trifluoromethyl radical, and n and p which may be the same or different, are each 1 or 2, and in which an alkyl radical or alkyl moiety has 1 to 4 carbon atoms in a straight or branched chain, or a pharmaceutically acceptable acid addition salt thereof.

2. A compound as claimed in claim 1 in which in general formula I the broken line forms, with the chain of four carbon atoms to which it is attached, a phenyl, naphthyl, pyridine, indolizine, pyrrolo[1,2-a]pyrazine or pyrrolo[1,2-a]pyrimidine ring system, R is hydrogen atom, R' is a hydrogen atom or a $C_{1-4}$ straight or branched chain alkyl radical, and n and p are each 1, or a pharmaceutically acceptable acid addition salt thereof.

3. A compound as claimed in claim 1 which is 3-[4-(4-methylbenzyl)-1-piperazinyl]biphenyl or a pharmaceutically acceptable acid addition salt thereof.

4. A compound as claimed in claim 1 which is 1-[4-(4-methylbenzyl)-1-piperazinyl]-3-phenylnaphthalene or a pharmaceutically acceptable acid addition salt thereof.

5. A compound as claimed in claim 1 which is 2-[4-(4-methylbenzyl)-1-piperazinyl]-4-phenylpyridine or a pharmaceutically acceptable acid addition salt thereof.

6. A compound as claimed in claim 1 which is 3-[4-(4-methylbenzyl)-1-piperazinyl]-1-phenylindolizine or a pharmaceutically acceptable acid addition salt thereof.

7. A compound as claimed in claim 1 which is 3-[4-(4-methylbenzyl)-1-piperazinyl]-1-phenylpyrrolo[1,2-a]pyrazine or a pharmaceutically acceptable acid addition salt thereof.

8. A compound as claimed in claim 1 which is 3-[4-(4-methylbenzyl)-1-piperazinyl]-1-phenylpyrrolo[1,2-a]pyrimidine or a pharmaceutically acceptable acid addition salt thereof.

9. An antipsychotic or neuroleptic pharmaceutical composition, which comprises a compound according to claim 1, and at least one diluent or adjuvant which is compatible and pharmaceutically acceptable.

10. A method of treatment of psychoses comprising administering to a subject suffering therefrom or liable thereto an effective amount of a compound as claimed in claim 1.

11. A method of treatment of psychoses comprising administering to a subject suffering therefrom or liable thereto an effective amount of a composition as claimed in claim 9.

12. A method of treatment according to claim 11 comprising administering orally sufficient composition to the subject to provide between 25 and 250 mg per day of a compound of formula I or pharmaceutically acceptable acid addition salt thereof.

* * * * *